United States Patent
Ostergaard et al.

(10) Patent No.: US 7,091,023 B2
(45) Date of Patent: Aug. 15, 2006

(54) **STEREOSELECTIVE ESTERASE FROM *ASPERGILLUS ORYZAE***

(75) Inventors: Peter Rahbek Ostergaard, Virum (DK); Carsten M. Hjort, Vaerlose (DK); Heinz-Josef Deussen, Soborg (DK); Magali Zundel, Soborg (DK); Soren Ebdrup, Roskilde (DK); Soren Christensen, Jyllinge (DK); Shamkant Anant Patkar, Lyngby (DK)

(73) Assignee: Novozymes A/S, Bagsvaerd (DK)

( * ) Notice: Subject to any disclaimer, the term of this patent is extended or adjusted under 35 U.S.C. 154(b) by 285 days.

(21) Appl. No.: 10/343,879

(22) PCT Filed: Jul. 19, 2001

(86) PCT No.: PCT/DK01/00508

§ 371 (c)(1),
(2), (4) Date: Feb. 5, 2003

(87) PCT Pub. No.: WO02/12472

PCT Pub. Date: Feb. 14, 2002

(65) Prior Publication Data

US 2003/0199048 A1  Oct. 23, 2003

Related U.S. Application Data

(63) Continuation-in-part of application No. 09/633,613, filed on Aug. 7, 2000, now abandoned, and a continuation-in-part of application No. 09/263,890, filed on Aug. 7, 2000, now abandoned.

(60) Provisional application No. 60/263,364, filed on Jan. 23, 2001.

(30) Foreign Application Priority Data

| Aug. 7, 2000 | (DK) | ..................... PCT/DK00/00439 |
| Aug. 7, 2000 | (DK) | ..................... PCT/DK00/00440 |
| Jan. 17, 2001 | (DK) | ................................ 200100088 |

(51) Int. Cl.
*C12N 9/16*   (2006.01)
*C12N 15/55*  (2006.01)
*C12P 7/40*   (2006.01)

(52) U.S. Cl. ...................... 435/196; 435/136; 435/280; 435/320.1; 435/252.3; 536/23.2

(58) Field of Classification Search ................ 435/196, 435/320.1, 252.3, 280, 136; 536/27.2
See application file for complete search history.

(56) References Cited

U.S. PATENT DOCUMENTS

| 4,587,462 A | 5/1986 | Buhrer |
| 5,155,028 A | 10/1992 | Fulling et al. |
| 5,516,679 A | 5/1996 | Chiang et al. |
| 5,665,584 A | 9/1997 | Hatamoto et al. |

FOREIGN PATENT DOCUMENTS

JP   A 7-206756   8/1995

OTHER PUBLICATIONS

Yoshioka, T.,et al. (1997) Eur. J. Biochem. 248, 58-62.*
Tenkanen, M. et al. (1995) J. Biotechnol. 42, 197-206.*
Guo, H.H., et al. (2004) Proc. Natl. Acad. Sci. USA 101(25), 9205-9210.*
Tenkanen et al., Journal of Biotechnology, vol. 18, pp. 69-84 (1991).
Tenkanen et al., Biotechnology and Applied Biochemistry, vol. 27 pp. 19-24, (1998).

* cited by examiner

*Primary Examiner*—Charles L. Patterson, Jr.
(74) *Attorney, Agent, or Firm*—Elias J. Lambiris (57) ABSTRACT

An esterase isolated from *Aspergillus oryzae* is capable of stereoselective hydrolysis of chiral esters and also has arylesterase activity (EC 3.1.1.2) and feruloyl esterase activity (EC 3.1.1.73). The esterase has only a limited homology to known amino acid sequences.

18 Claims, 1 Drawing Sheet

SEQUENCE LISTING

<160> NUMBER OF SEQ ID NOS: 27

<210> SEQ ID NO 1
<211> LENGTH: 2346
<212> TYPE: DNA
<213> ORGANISM: Aspergillus oryzae
<220> FEATURE:
<221> NAME/KEY: misc_feature
<222> LOCATION: (31)..()
<223> OTHER INFORMATION: n is unknown
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: CDS
<222> LOCATION: (572)..(911)
<220> FEATURE:
<221> NAME/KEY: sig_peptide
<222> LOCATION: (572)..(628)
<220> FEATURE:
<221> NAME/KEY: mat_peptide
<222> LOCATION: (629)..()
<220> FEATURE:
<221> NAME/KEY: CDS
<222> LOCATION: (971)..(2208)

<400> SEQUENCE: 1

```
ttacttcacc aggatttagg gtcgagttcc ntcggtgccg aaaagaatgc ccgagcaatg      60
tatttatgtg gccccaggac agtttaattg ccgatatcca agccttcag gtgagtaaat     120 tgcagagcgt gtgacaaggg taaccaggag aatactccgc attttgtggg aaccccatg     180 ggacgatctt tgggatgtgg agacactcat ttgaaaatga cagtgacttg tccagtcagc    240
gctgctgaaa attgtctccc taatcccggc ttttccttgt cgaaaatgat tggggagtgc    300
gtcacgtcac ggccaagctt tcctgcttag gaatttccta agctaataca tggtaccttc    360
ctccggtcaa acttcggaga agccctagat aagggcacgg gatatagtcc gatcttcatg    420
taccgacgga ttgaaagttt gaaacgctaa atgacatgtt ccttagtact gtcagcagtc    480
tccggtatct ccgaggcagc tacatatata aagtcaccaa gctcacggca gaggaaaatg    540
tctccgtgaa caacaaccac acccagccag t atg cct tca ctt cgc cgg ctt       592
                                   Met Pro Ser Leu Arg Arg Leu
                                                          -15 ctg cct ttt ctt gct gca ggc tcc gcc gct ctg gca agc caa gat acg      640
Leu Pro Phe Leu Ala Ala Gly Ser Ala Ala Leu Ala Ser Gln Asp Thr
        -10              -5              -1  1 ttt caa ggc aag tgt act ggt ttt gca gac aag ata aac ctg cct aat      688
Phe Gln Gly Lys Cys Thr Gly Phe Ala Asp Lys Ile Asn Leu Pro Asn
 5               10              15              20 gtg cgg gta aat ttt gtc aat tac gtg cct gga ggc acc aat ctt tct      736
Val Arg Val Asn Phe Val Asn Tyr Val Pro Gly Gly Thr Asn Leu Ser
             25              30              35 ttg cca gat aat ccc acc agc tgc ggc aca acc tct caa gta gtg tcc      784
Leu Pro Asp Asn Pro Thr Ser Cys Gly Thr Thr Ser Gln Val Val Ser
         40              45              50
```

-continued

| | |
|---|---|
| gag gat gtc tgc cgt att gcc atg gct gtt gca acc tca aac agt agc<br>Glu Asp Val Cys Arg Ile Ala Met Ala Val Ala Thr Ser Asn Ser Ser<br>       55                    60                    65 | 832 |
| gaa atc acc ctt gaa gca tgg ctc cca caa aac tac act ggt cgt ttc<br>Glu Ile Thr Leu Glu Ala Trp Leu Pro Gln Asn Tyr Thr Gly Arg Phe<br>     70                    75                    80 | 880 |
| ctg agt acg ggc aac ggt ggt ctc tca ggc t gtatgttcta cccggcaccg<br>Leu Ser Thr Gly Asn Gly Gly Leu Ser Gly<br>85                    90 | 931 |
| cgatgcgaca tggcacaact tcaaactaac gtcttacag gt   att cag tac tat<br>                                                               Cys Ile Gln Tyr Tyr<br>                                                                         95 | 984 |
| gat cta gcg tac acc tcc ggc ctc ggg ttt gcc acg gtt ggc gcc aac<br>Asp Leu Ala Tyr Thr Ser Gly Leu Gly Phe Ala Thr Val Gly Ala Asn<br>100                       105                     110                     115 | 1032 |
| agc ggc cat aac gga aca tcc ggg gag cct ttc tac cac cac cca gag<br>Ser Gly His Asn Gly Thr Ser Gly Glu Pro Phe Tyr His His Pro Glu<br>                    120                     125                     130 | 1080 |
| gtc ctc gaa gac ttt gta cat cgt tca gtc cac act ggt gtc gtg gtt<br>Val Leu Glu Asp Phe Val His Arg Ser Val His Thr Gly Val Val Val<br>                 135                     140                     145 | 1128 |
| gga aag caa ttg aca aag ctt ttc tac gag gaa ggg ttc aag aag tcg<br>Gly Lys Gln Leu Thr Lys Leu Phe Tyr Glu Glu Gly Phe Lys Lys Ser<br>                 150                     155                     160 | 1176 |
| tac tac ctt ggt tgc tcc act ggt ggt cgg cag ggc ttt aaa tcc gtc<br>Tyr Tyr Leu Gly Cys Ser Thr Gly Gly Arg Gln Gly Phe Lys Ser Val<br>     165                    170                     175 | 1224 |
| cag aaa tat ccc aat gac ttt gat ggt gtt gta gcc ggt gca ccg gca<br>Gln Lys Tyr Pro Asn Asp Phe Asp Gly Val Val Ala Gly Ala Pro Ala<br>180                       185                     190                     195 | 1272 |
| ttc aat atg atc aac ctc atg tca tgg agt gcc cac ttc tat tca atc<br>Phe Asn Met Ile Asn Leu Met Ser Trp Ser Ala His Phe Tyr Ser Ile<br>                 200                     205                     210 | 1320 |
| acg ggg cca gtt ggg tcc gac aca tac cta tcc cct gac ctg tgg aat<br>Thr Gly Pro Val Gly Ser Asp Thr Tyr Leu Ser Pro Asp Leu Trp Asn<br>                 215                     220                     225 | 1368 |
| atc acc cat aag gag atc ctg cgt caa tgc gac ggt atc gat gga gca<br>Ile Thr His Lys Glu Ile Leu Arg Gln Cys Asp Gly Ile Asp Gly Ala<br>                 230                     235                     240 | 1416 |
| gag gac ggc att att gaa gac cca agt ctt tgc agc ccg gtt ctt gaa<br>Glu Asp Gly Ile Ile Glu Asp Pro Ser Leu Cys Ser Pro Val Leu Glu<br>245                       250                     255 | 1464 |
| gcg atc atc tgc aag cct ggt caa aac act acc gag tgt tta act ggc<br>Ala Ile Ile Cys Lys Pro Gly Gln Asn Thr Thr Glu Cys Leu Thr Gly<br>260                       265                     270                     275 | 1512 |
| aag caa gcc cat acc gtt cgc gaa att ttc tcc ccg ctg tac gga gtg<br>Lys Gln Ala His Thr Val Arg Glu Ile Phe Ser Pro Leu Tyr Gly Val<br>                 280                     285                     290 | 1560 |
| aac ggc acc ttg ctt tat ccc cgc atg cag cct ggc tct gag gtg atg<br>Asn Gly Thr Leu Leu Tyr Pro Arg Met Gln Pro Gly Ser Glu Val Met<br>                    295                     300                     305 | 1608 |
| gct tct tcc ata atg tac aac ggc cag cct ttc cag tat agc gca gac<br>Ala Ser Ser Ile Met Tyr Asn Gly Gln Pro Phe Gln Tyr Ser Ala Asp<br>                    310                     315                     320 | 1656 |
| tgg tac cgc tat gtt gtc tac gag aac ccc aac tgg gat gca acc aag<br>Trp Tyr Arg Tyr Val Val Tyr Glu Asn Pro Asn Trp Asp Ala Thr Lys<br>     325                    330                     335 | 1704 |
| ttc tcc gtc cgt gac gca gcc gtc gct ttg aag cag aac cca ttc aat<br>Phe Ser Val Arg Asp Ala Ala Val Ala Leu Lys Gln Asn Pro Phe Asn<br>340                       345                     350                     355 | 1752 |

```
ctc cag acc tgg gac gca gat atc tcc tct ttc cgc aag gca ggc ggt   1800
Leu Gln Thr Trp Asp Ala Asp Ile Ser Ser Phe Arg Lys Ala Gly Gly
            360                 365                 370 aaa gtc ctc acc tac cac ggt ctc atg gat caa ctt atc agc tcg gag   1848
Lys Val Leu Thr Tyr His Gly Leu Met Asp Gln Leu Ile Ser Ser Glu
        375                 380                 385 aac tcc aag ctt tac tat gcg cgc gtt gcg gaa acc atg aac gtc cct   1896
Asn Ser Lys Leu Tyr Tyr Ala Arg Val Ala Glu Thr Met Asn Val Pro
        390                 395                 400 ccg gaa gag ctg gac gag ttc tac cgc ttc ttt cag atc agt gga atg   1944
Pro Glu Glu Leu Asp Glu Phe Tyr Arg Phe Phe Gln Ile Ser Gly Met
    405                 410                 415 gcc cat tgc agt gga ggt gac gga gcg tac ggc att gga aac cag ctc   1992
Ala His Cys Ser Gly Gly Asp Gly Ala Tyr Gly Ile Gly Asn Gln Leu
420                 425                 430                 435 gtg acc tat aac gat gcc aat cct gaa aac aac gtc ctc atg gct atg   2040
Val Thr Tyr Asn Asp Ala Asn Pro Glu Asn Asn Val Leu Met Ala Met
                440                 445                 450 gtt cag tgg gtg gag aag ggc atc gcc ccg gag acc att cgt ggt gct   2088
Val Gln Trp Val Glu Lys Gly Ile Ala Pro Glu Thr Ile Arg Gly Ala
            455                 460                 465 aag ttt acc aat ggc acg ggc tcg gcc gtg gag tat act cgc aag cac   2136
Lys Phe Thr Asn Gly Thr Gly Ser Ala Val Glu Tyr Thr Arg Lys His
        470                 475                 480 tgc cgc tac cct cgc agg aat gta tac aag ggg cca ggg aac tac act   2184
Cys Arg Tyr Pro Arg Arg Asn Val Tyr Lys Gly Pro Gly Asn Tyr Thr
        485                 490                 495 gat gag aat gcc tgg caa tgt gtt taaattgttg aagtattgta catatatttg   2238
Asp Glu Asn Ala Trp Gln Cys Val
500                 505 ctcatagagg caagacgttt gcatgtcttg ataattattt attcgcccat catagcagat   2298
agaatataag accacgtcct acgaaactcg cagtgcactt gtataatt              2346

<210> SEQ ID NO 2
<211> LENGTH: 526
<212> TYPE: PRT
<213> ORGANISM: Aspergillus oryzae

<400> SEQUENCE: 2

Met Pro Ser Leu Arg Arg Leu Leu Pro Phe Leu Ala Ala Gly Ser Ala
                -15                 -10                  -5

Ala Leu Ala Ser Gln Asp Thr Phe Gln Gly Lys Cys Thr Gly Phe Ala
         -1  1                   5                  10

Asp Lys Ile Asn Leu Pro Asn Val Arg Val Asn Phe Val Asn Tyr Val
        15                  20                  25

Pro Gly Gly Thr Asn Leu Ser Leu Pro Asp Asn Pro Thr Ser Cys Gly
30                  35                  40                  45

Thr Thr Ser Gln Val Val Ser Glu Asp Val Cys Arg Ile Ala Met Ala
                50                  55                  60

Val Ala Thr Ser Asn Ser Ser Glu Ile Thr Leu Glu Ala Trp Leu Pro
            65                  70                  75

Gln Asn Tyr Thr Gly Arg Phe Leu Ser Thr Gly Asn Gly Gly Leu Ser
        80                  85                  90

Gly Cys Ile Gln Tyr Tyr Asp Leu Ala Tyr Thr Ser Gly Leu Gly Phe
    95                 100                 105

Ala Thr Val Gly Ala Asn Ser Gly His Asn Gly Thr Ser Gly Glu Pro
110                 115                 120                 125
```

```
Phe Tyr His His Pro Glu Val Leu Glu Asp Phe Val His Arg Ser Val
                130                 135                 140

His Thr Gly Val Val Gly Lys Gln Leu Thr Lys Leu Phe Tyr Glu
            145                 150                 155

Glu Gly Phe Lys Lys Ser Tyr Tyr Leu Gly Cys Ser Thr Gly Gly Arg
            160                 165                 170

Gln Gly Phe Lys Ser Val Gln Lys Tyr Pro Asn Asp Phe Asp Gly Val
        175                 180                 185

Val Ala Gly Ala Pro Ala Phe Asn Met Ile Asn Leu Met Ser Trp Ser
190                 195                 200                 205

Ala His Phe Tyr Ser Ile Thr Gly Pro Val Gly Ser Asp Thr Tyr Leu
                210                 215                 220

Ser Pro Asp Leu Trp Asn Ile Thr His Lys Glu Ile Leu Arg Gln Cys
            225                 230                 235

Asp Gly Ile Asp Gly Ala Glu Asp Gly Ile Ile Glu Asp Pro Ser Leu
        240                 245                 250

Cys Ser Pro Val Leu Glu Ala Ile Ile Cys Lys Pro Gly Gln Asn Thr
        255                 260                 265

Thr Glu Cys Leu Thr Gly Lys Gln Ala His Thr Val Arg Glu Ile Phe
270                 275                 280                 285

Ser Pro Leu Tyr Gly Val Asn Gly Thr Leu Leu Tyr Pro Arg Met Gln
                290                 295                 300

Pro Gly Ser Glu Val Met Ala Ser Ser Ile Met Tyr Asn Gly Gln Pro
            305                 310                 315

Phe Gln Tyr Ser Ala Asp Trp Tyr Arg Tyr Val Val Tyr Glu Asn Pro
        320                 325                 330

Asn Trp Asp Ala Thr Lys Phe Ser Val Arg Asp Ala Ala Val Ala Leu
        335                 340                 345

Lys Gln Asn Pro Phe Asn Leu Gln Thr Trp Asp Ala Asp Ile Ser Ser
350                 355                 360                 365

Phe Arg Lys Ala Gly Gly Lys Val Leu Thr Tyr His Gly Leu Met Asp
                370                 375                 380

Gln Leu Ile Ser Ser Glu Asn Ser Lys Leu Tyr Tyr Ala Arg Val Ala
            385                 390                 395

Glu Thr Met Asn Val Pro Pro Glu Glu Leu Asp Glu Phe Tyr Arg Phe
            400                 405                 410

Phe Gln Ile Ser Gly Met Ala His Cys Ser Gly Gly Asp Gly Ala Tyr
        415                 420                 425

Gly Ile Gly Asn Gln Leu Val Thr Tyr Asn Asp Ala Asn Pro Glu Asn
430                 435                 440                 445

Asn Val Leu Met Ala Met Val Gln Trp Val Glu Lys Gly Ile Ala Pro
                450                 455                 460

Glu Thr Ile Arg Gly Ala Lys Phe Thr Asn Gly Thr Gly Ser Ala Val
            465                 470                 475

Glu Tyr Thr Arg Lys His Cys Arg Tyr Pro Arg Arg Asn Val Tyr Lys
        480                 485                 490

Gly Pro Gly Asn Tyr Thr Asp Glu Asn Ala Trp Gln Cys Val
        495                 500                 505

<210> SEQ ID NO 3
<211> LENGTH: 18
<212> TYPE: PRT
<213> ORGANISM: Aspergillus oryzae
<220> FEATURE:
```

```
<221> NAME/KEY: misc_feature
<223> OTHER INFORMATION: 161299Afr15

<400> SEQUENCE: 3

Val Leu Thr Tyr His Gly Leu Met Asp Gln Leu Ile Ser Ser Glu Asn
1               5                   10                  15
Ser Lys

<210> SEQ ID NO 4
<211> LENGTH: 18
<212> TYPE: PRT
<213> ORGANISM: Aspergillus oryzae
<220> FEATURE:
<221> NAME/KEY: misc_feature
<223> OTHER INFORMATION: 161299Afr17

<400> SEQUENCE: 4

Gln Asn Pro Phe Asn Leu Gln Thr Trp Asp Ala Asp Ile Ser Ser Phe
1               5                   10                  15
Arg Lys

<210> SEQ ID NO 5
<211> LENGTH: 21
<212> TYPE: PRT
<213> ORGANISM: Aspergillus oryzae
<220> FEATURE:
<221> NAME/KEY: misc_feature
<223> OTHER INFORMATION: 161299Afr23

<400> SEQUENCE: 5

Tyr Pro Asn Asp Phe Asp Gly Val Val Ala Gly Ala Pro Ala Phe Asn
1               5                   10                  15
Met Ile Asn Leu Met
            20

<210> SEQ ID NO 6
<211> LENGTH: 27
<212> TYPE: DNA
<213> ORGANISM: Artificial Sequence
<220> FEATURE:
<221> NAME/KEY: misc_feature
<223> OTHER INFORMATION: B2716F09

<400> SEQUENCE: 6
cccgccttca acatgatcaa cctsatg                                     27

<210> SEQ ID NO 7
<211> LENGTH: 26
<212> TYPE: DNA
<213> ORGANISM: Artificial Sequence
<220> FEATURE:
<221> NAME/KEY: misc_feature
<223> OTHER INFORMATION: B2716F11

<400> SEQUENCE: 7
atsagctggt ccatsagrcc gtgrta                                      26

<210> SEQ ID NO 8
<211> LENGTH: 24
<212> TYPE: DNA
<213> ORGANISM: Artificial Sequence
<220> FEATURE:
<221> NAME/KEY: misc_feature
<223> OTHER INFORMATION: -48 reverse

<400> SEQUENCE: 8
```

-continued agcggataac aatttcacac agga                                      24

<210> SEQ ID NO 9
<211> LENGTH: 17
<212> TYPE: DNA
<213> ORGANISM: Artificial Sequence
<220> FEATURE:
<221> NAME/KEY: misc_feature
<223> OTHER INFORMATION: -40 universal

<400> SEQUENCE: 9
gttttcccag tcacgac                                              17

<210> SEQ ID NO 10
<211> LENGTH: 22
<212> TYPE: DNA
<213> ORGANISM: Artificial Sequence
<220> FEATURE:
<221> NAME/KEY: misc_feature
<223> OTHER INFORMATION: B2998F06

<400> SEQUENCE: 10
ccccgtgatt gaatagaagt gg                                        22

<210> SEQ ID NO 11
<211> LENGTH: 22
<212> TYPE: DNA
<213> ORGANISM: Artificial Sequence
<220> FEATURE:
<221> NAME/KEY: misc_feature
<223> OTHER INFORMATION: B3591G12

<400> SEQUENCE: 11
tccataatgt acaacggcca gc                                        22

<210> SEQ ID NO 12
<211> LENGTH: 22
<212> TYPE: DNA
<213> ORGANISM: Artificial Sequence
<220> FEATURE:
<221> NAME/KEY: misc_feature
<223> OTHER INFORMATION: B2998F07

<400> SEQUENCE: 12
gacgcagata tctcctcttt cc                                        22

<210> SEQ ID NO 13
<211> LENGTH: 21
<212> TYPE: DNA
<213> ORGANISM: Artificial Sequence
<220> FEATURE:
<221> NAME/KEY: misc_feature
<223> OTHER INFORMATION: B3864E07

<400> SEQUENCE: 13
gattggtgcc tccaggcacg t                                         21

<210> SEQ ID NO 14
<211> LENGTH: 21
<212> TYPE: DNA
<213> ORGANISM: Artificial Sequence
<220> FEATURE:
<221> NAME/KEY: misc_feature
<223> OTHER INFORMATION: B3864E08

<400> SEQUENCE: 14

-continued

```
gcaagtgtac tggttttgca g                                          21

<210> SEQ ID NO 15
<211> LENGTH: 21
<212> TYPE: DNA
<213> ORGANISM: Artificial Sequence
<220> FEATURE:
<221> NAME/KEY: misc_feature
<223> OTHER INFORMATION: B3998D09

<400> SEQUENCE: 15
ttatcaagac atgcaaacgt c                                          21

<210> SEQ ID NO 16
<211> LENGTH: 20
<212> TYPE: DNA
<213> ORGANISM: Artificial Sequence
<220> FEATURE:
<221> NAME/KEY: misc_feature
<223> OTHER INFORMATION: B3998D10

<400> SEQUENCE: 16
cttggttgct ccactggtgg                                            20

<210> SEQ ID NO 17
<211> LENGTH: 20
<212> TYPE: DNA
<213> ORGANISM: Artificial Sequence
<220> FEATURE:
<221> NAME/KEY: misc_feature
<223> OTHER INFORMATION: B3998D11

<400> SEQUENCE: 17
tccagctctt ccgagggac                                             20

<210> SEQ ID NO 18
<211> LENGTH: 22
<212> TYPE: DNA
<213> ORGANISM: Artificial Sequence
<220> FEATURE:
<221> NAME/KEY: misc_feature
<223> OTHER INFORMATION: B3591G11

<400> SEQUENCE: 18
aaagcaaggt gccgttcact cc                                         22

<210> SEQ ID NO 19
<211> LENGTH: 11
<212> TYPE: DNA
<213> ORGANISM: Artificial Sequence
<220> FEATURE:
<221> NAME/KEY: misc_feature
<223> OTHER INFORMATION: Pna2/tpi nucleotide 134-144

<400> SEQUENCE: 19
gtactaaaac c                                                     11

<210> SEQ ID NO 20
<211> LENGTH: 11
<212> TYPE: DNA
<213> ORGANISM: Artificial Sequence
<220> FEATURE:
<221> NAME/KEY: misc_feature
<223> OTHER INFORMATION: Pna2/tpi nucleotide 134-144 altered

<400> SEQUENCE: 20
ccgttaaatt t                                                     11
```

<210> SEQ ID NO 21
<211> LENGTH: 45
<212> TYPE: DNA
<213> ORGANISM: Artificial Sequence
<220> FEATURE:
<221> NAME/KEY: misc_feature
<223> OTHER INFORMATION: 141223

<400> SEQUENCE: 21
ggatgctgtt gactccggaa atttaacggt ttggtcttgc atccc                45

<210> SEQ ID NO 22
<211> LENGTH: 14
<212> TYPE: DNA
<213> ORGANISM: Artificial Sequence
<220> FEATURE:
<221> NAME/KEY: misc_feature
<223> OTHER INFORMATION: Pna2/tpi 423-436

<400> SEQUENCE: 22
atgcaattta aact                14

<210> SEQ ID NO 23
<211> LENGTH: 14
<212> TYPE: DNA
<213> ORGANISM: Artificial Sequence
<220> FEATURE:
<221> NAME/KEY: misc_feature
<223> OTHER INFORMATION: Pna2/tpi nucleotide 423-436 altered

<400> SEQUENCE: 23
cggcaattta acgg                14

<210> SEQ ID NO 24
<211> LENGTH: 44
<212> TYPE: DNA
<213> ORGANISM: Artificial Sequence
<220> FEATURE:
<221> NAME/KEY: misc_feature
<223> OTHER INFORMATION: 141222

<400> SEQUENCE: 24
ggtattgtcc tgcagacggc aatttaacgg cttctgcgaa tcgc                44

<210> SEQ ID NO 25
<211> LENGTH: 34
<212> TYPE: DNA
<213> ORGANISM: Artificial Sequence
<220> FEATURE:
<221> NAME/KEY: misc_feature
<223> OTHER INFORMATION: B6093H05

<400> SEQUENCE: 25
ttggatcctt caccatgcct tcacttcgcc ggct                34

<210> SEQ ID NO 26
<211> LENGTH: 30
<212> TYPE: DNA
<213> ORGANISM: Artificial Sequence
<220> FEATURE:
<221> NAME/KEY: misc_feature
<223> OTHER INFORMATION: B6093H03

<400> SEQUENCE: 26
atctcgagtt taaacacatt gccaggcatt                30

```
<210> SEQ ID NO 27
<211> LENGTH: 572
<212> TYPE: DNA
<213> ORGANISM: Aspergillus oryzae
<220> FEATURE:
<221> NAME/KEY: misc_feature
<223> OTHER INFORMATION: PCR fragment

<400> SEQUENCE: 27
cccgccttca acatgatcaa cctgatgtca tggagtgccc acttctattc aatcacgggg        60
ccagttgggt ccgacacata cctatcccct gacctgtgga atatcaccca taaggagatc       120
ctgcgtcaat gcgacggtat cgatggagca gaggacggca ttattgaaga cccaagtctt       180
tgcagcccgg ttcttgaagc gatcatctgc aagcctggtc aaaacactac cgagtgttta       240
actggcaagc aagcccatac cgttcgcgaa attttctccc cgctgtacgg agtgaacggc       300
accttgcttt atccccgcat gcagcctggc tctgaggtga tggcttcttc cataatgtac       360
aacggccagc ctttccagta tagcgcagac tggtaccgct atgttgtcta cgagaacccc       420
aactgggatg caaccaagtt ctccgtccgt gacgcagccg tcgctttgaa gcagaaccca       480
ttcaayctcc agacctggga cgcagatatc tcctctttcc gcaaggcagg cggtaaagtc       540
ctcacctatc acggcctgat ggaccagctg at                                     572
```

STEREOSELECTIVE ESTERASE FROM ASPERGILLUS ORYZAE

This application is a 35 U.S.C. 371 national application of PCT/DK/01/00508 filed Jul. 19, 2001, which is a continuation-in-part of U.S. application Nos. 09/633,613 now abandoned and 09/633,890, now abandoned both filed Aug. 7, 2000 and claims priority or the benefit under 35 U.S.C. 119 of PCT application nos. PCT/DK00/00439 and PCT/DK00/00440, Danish application no. PA 2001 00088, and U.S. provisional application No. 60/263,364 filed Aug. 7, 2000, Aug. 7, 2000, Jan. 17, 2001, and Jan. 23, 2001, respectively, the contents of which are fully incorporated herein by reference.

FIELD OF THE INVENTION

The present invention relates to an esterase, to methods of using and producing it, and to a nucleic acid sequence encoding it. The esterase is capable of stereoselective hydrolysis of chiral esters and of hydrolyzing ferulic acid esters.

BACKGROUND OF THE INVENTION

It is known to prepare chiral esters of high optical purities by asymmetric hydrolysis with enzymes. Thus, U.S. Pat. No. 4,587,462 discloses asymmetric hydrolysis of lower alkyl esters of naproxen with a microbial enzyme, particularly a specific splitting esterase from *Aspergillus oryzae* DSM 2808 (ATCC 11492). U.S. Pat. No. 5,155,028 discloses enzymatic stereoselective ester cleavage using lipases, esterases or proteases, e.g. lipases or esterases from *Aspergillus* or proteases from *Aspergillus oryzae*. JP 7-206756 A discloses use of an enzyme to prepare optically active compounds. The enzyme may be a protease or esterase produced by *Aspergillus*, e.g. from *A. oryzae*.

Enzymes with ferulic acid esterase activity are known, e.g., from *Aspergillus oryzae*. M. Tenkanen, Biotechnology and Applied Biochemistry, 27 (1), 19–24 (1998)); M. Tenkanen et al., J. Biotechnol., 18 (1–2), 69–84 (1991).

U.S. Pat. No. 5,516,679 discloses a penicillin V amidohydrolase from *Fusarium oxysporum*.

SUMMARY OF THE INVENTION

The inventors have isolated an esterase from *Aspergillus oryzae* which is capable of stereoselective hydrolysis of chiral esters and also has arylesterase activity (EC 3.1.1.2) and feruloyl esterase activity (EC 3.1.1.73). The novel esterase has only a limited homology to known amino acid sequences. The inventors also isolated a gene encoding the novel esterase and cloned it into an *E. coli* strain.

Accordingly, the invention provides an esterase which may be a polypeptide having an amino acid sequence as the mature peptide shown in SEQ ID NO: 2 or which can be obtained therefrom by substitution, deletion, and/or insertion of one or more amino acids.

Further, the esterase of the invention may be a polypeptide encoded by the esterase encoding part of the DNA sequence cloned into a plasmid present in *Escherichia coli* deposit number DSM 13977.

The esterase may also be an analogue of the polypeptide defined above which:

i) has at least 50% identity with said polypeptide, ii) is immunologically reactive with an antibody raised against said polypeptide in purified form, iii) is an allelic variant of said polypeptide, Finally, the esterase of the invention may be a polypeptide which is encoded by a nucleic acid sequence which hybridizes at 60° C., 2×SSC, 0.5% SDS with the complementary strand of nucleotides 572–911 and 971–2208 of SEQ ID NO: 1 or a subsequence thereof of at least 100 nucleotides.

The nucleic acid sequence of the invention may comprise a nucleic acid sequence which encodes the esterase described above, or it may encode an esterase and comprise:

a) the esterase encoding part of the DNA sequence cloned into a plasmid present in *Escherichia coli* DSM 13977, b) nucleotides 629–911 and 971–2208 of SEQ ID NO: 1 (encoding the mature polypeptide), or c) an analogue of the DNA sequence defined in a) or b) which i) has at least 60% identity with said DNA sequence, or ii) hybridizes at 60° C., 2×SSC, 0.5% SDS with the complementary sequence of said DNA sequence.

Other aspects of the invention provide a recombinant expression vector comprising the DNA sequence, and a cell transformed with the DNA sequence or the recombinant expression vector.

A comparison with full-length prior-art sequences shows the closest known sequence is a penicillin V amidohydrolase from *Fusarium oxysporum* (U.S. Pat. No. 5,516,679). The mature amino acid sequence of the invention has 48% identity to the known sequence, and the corresponding DNA sequences have 54% identity.

DETAILED DESCRIPTION OF THE INVENTION

Genomic DNA Source

The esterase of the invention may be derived from strains of *Aspergillus*, particularly strains of *A. oryzae*, using probes designed on the basis of the DNA sequence in this specification.

A strain of *Escherichia coli* containing a gene encoding the esterase was deposited by the inventors under the terms of the Budapest Treaty with the DSMZ Deutsche Sammlung von Microorganismen und Zellkulturen GmbH, Mascheroder Weg 1b, D-38124 Braunschweig DE on 11 Jan. 2001 under accession number DSM 13977

Recombinant Expression Vector

The expression vector of the invention typically includes control sequences encoding a promoter, operator, ribosome binding site, translation initiation signal, and, optionally, a selectable marker, a transcription terminator, a repressor gene or various activator genes. The vector may be an autonomously replicating vector, or it may be integrated into the host cell genome.

Production by Cultivation of Transformant

The esterase of the invention may be produced by transforming a suitable host cell with a DNA sequence encoding the esterase, cultivating the transformed organism under conditions permitting the production of the enzyme, and recovering the enzyme from the culture.

The host organism may be a eukaryotic cell, in particular a fungal cell, such as a yeast cell or a filamentous fungal cell, such as a strain of *Aspergillus*, *Fusarium*, *Trichoderma* or *Saccharomyces*, particularly *A. niger*, *A. oryzae*, *F.*

*graminearum, F. sambucinum, F. cerealis* or *S. cerevisiae*. The production of the esterase in such host organisms may be done by the general methods described in EP 238,023 (Novo Nordisk), WO 96/00787 (Novo Nordisk) or EP 244,234 (Alko).

Properties and Uses of Esterase

The esterase of the invention is capable of stereoselective hydrolysis of esters including substituted esters of 3-phenyl-propanoic acids. It does not hydrolyse naproxen ethyl ester.

The esterase is useful for the preparation of optically enriched esters or acids, e.g. substituted esters of 3-phenyl-propanoic acids and substituted 3-phenyl-propanoic acids for pharmaceutical use.

The esterase also has arylesterase activity (EC 3.1.1.2) and feruloyl esterase activity (EC 3.1.1.73) and is useful in hydrolyzing feruloyl esters into ferulic acid and alcohol. It is useful for the release of ferulic acid bound to hemicellulose in the degradation of plant material and plant cell walls, e.g. as described in GB 2301103 and WO 200014234. It may also be used for the production of vanillic acid in analogy with U.S. Pat. No. 5,955,137.

Hybridization

The hybridization is used to indicate that a given DNA sequence is analogous to a nucleotide probe corresponding to a DNA sequence of the invention. The hybridization conditions are described in detail below.

Suitable conditions for determining hybridization between a nucleotide probe and a homologous DNA or RNA sequence involves presoaking of the filter containing the DNA fragments or RNA to hybridize in 5×SSC (standard saline citrate) for 10 min, and prehybridization of the filter in a solution of 5×SSC (Sambrook et al. 1989), 5× Denhardt's solution (Sambrook et al. 1989), 0.5% SDS and 100 µg/ml of denatured sonicated salmon sperm DNA (Sambrook et al. 1989), followed by hybridization in the same solution containing a random-primed (Feinberg, A. P. and Vogelstein, B. (1983) *Anal. Biochem.* 132:6–13), $^{32}$P-dCTP-labeled (specific activity>1×10$^9$ cpm/µg) probe for 12 hours at approx. 60° C. The filter is then washed two times for 30 minutes in 2×SSC, 0.5% SDS at a temperature of 60° C., more preferably at least 65° C., even more preferably at least 68° C.

Molecules to which the oligonucleotide probe hybridizes under these conditions are detected using a x-ray film.

Alignment and Homology

The esterase and the nucleotide sequence of the invention preferably have homologies to the disclosed sequences of at least 80% identity, particularly at least 90% identity or at least 95% identity, e.g. at least 98% identity.

For purposes of the present invention, alignments of sequences and calculation of identityscores were done using a Clustal W (J. D. Thompson et al (1994) NAR 22 (22) p 4673–4680) alignment, useful for both protein and DNA alignments. The default scoring matrices Blosum62mt2and swgapdnamt are used for protein and DNA alignments respectively. The gap opening penalty is 10 and the gap extension penalty: 0,1 for proteins.—The gap opening penalty is 15 and the gap extension penalty is 6,66 for DNA. The alignments were done using the computer programme allignX which is a component of the Vector NTI Suite 6.0 package from Informax, Inc (www.informax.com))

EXAMPLES

Example 1

Preparation of a Crude Esterase Preparation from *Aspergillus oryzae*

*Aspergillus oryzae* IFO4177 was fermented using a fed-batch process with maltose/maltodextrin or glucose as the main carbon source. The batch medium contained: maltose/maltodextrin, ammonium sulphate, potassium-dihydrogen-phosphate, yeast extract, beech xylan, MgSO4,7H2O, citric acid, potassium sulphate, trace metal solution and an anti-foam agent. All these components were used in concentrations all being within the range of 1–18 g/L final medium. The medium pH was kept at 4.5 throughout the fermentation. The feed consisted of maltose/maltodextrin or glucose in the range of 280 g/L. 6.5 kg of batch medium was inoculated with 500 mL of seed culture. After 15–25 hours of batch fermentation the addition of feed was initiated using a feed addition rate of 15–25 g of feed per hour. This fed-batch state was continued for 100–160 hour of fermentation. Dissolved oxygen above 50% saturation was maintained by means of closed-loop control of the agitation rate. Aeration was kept at 1 volume air per volume batch medium per hour. A headspace pressure of 0.5 bar over-pressure was maintained throughout the entire fermentation. After harvest of the broth, both biomass and un-dissolved matter was removed in a filtration step. The supernatant was concentrated by removal of water using ultrafiltration, evaporation or freeze drying.

Example 2

Preparation of (2S)-2-Ethoxy-3-(4-hydroxyphenyl) propanoic acid and Ethyl (2R)-2-Ethoxy-3-(4-hydroxyphenyl)propanoate Ethyl (2RS) (+/−) 2-ethoxy-3-(4-hydroxyphenyl)propanoate (0.5 g) was shaken with 60 mg of the lyophilised esterase preparation from *Aspergillus oryzae* in 1 ml 1M phosphate buffer (pH=7) with organic co-solvents (according to the table below) at 27° C. The reaction mixture was poured into 20 ml MeOH after 4 h to stop the enzymatic reactions followed by analysis by chiral capillary electrophoresis to determine the enantiomeric excess (ee) as follows:

HP 3D Capillary Electrophoresis and 80.5/72.0 cm, 50 mm HP bubble capillary were used. The electrolyte was HS-β-CD (Regis) (2% w/v) and TM-β-CD (Sigma) (2% w/v) in 25 mM borate buffer pH 9.3 (HP). The reaction mixture was diluted approximately 25 times in borate buffer 5 mM, pH 9.3 (or final concentration ca. 0.025 mg/ml–0.1 mg/ml) and injected (50 mbar in 4.0 seconds). The applied voltage was 30 kV.

| Co-solvent | Product$_{acid}$ (%) | (ee)$_{acid}$ (%) |
|---|---|---|
| Acetone/0.1 ml | 37 | 93 |
| Acetone/0.3 ml | 31 | 94 |
| THF/0.1 ml | 36 | 94 |
| THF/0.2 ml | 31 | 93 |
| THF/0.3 ml | 21 | 91 |
| 2-Propanol/0.1 ml | 36 | 97 |
| 2-Propanol/0.3 ml | 27 | 93 |
| Ethanol/0.1 ml | 35 | 96 |

-continued

| Co-solvent | Product$_{acid}$ (%) | (ee)$_{acid}$ (%) |
|---|---|---|
| Ethanol/0.2 ml | 32 | 96 |
| Ethanol/0.3 ml | 22 | 93 |

Example 3

Preparation of (2S)-2-Ethoxy-3-(4-hydroxyphenyl) propanoic acid and Ethyl (2R)-2-Ethoxy-3-(4-hydroxyphenyl)Propanoate Ethyl (2R/S) (+/−) 2-ethoxy-3-(4-hydroxyphenyl)propanoate (5 g) was added to an aqueous 0.1 M phosphate buffer pH 7 (10 ml). 100 mg of the lyophilised esterase preparation from Aspergillus oryzae was added and the mixture was stirred for 18 hours at room temperature. During that time, the pH of the reaction mixture was kept constant at pH=6-8 by addition of NaOH. Most of the water was evaporated in vacuo. Methanol was added to the remaining slurry in order to stop the hydrolysis. The precipitate, which formed was filtered off and the methanol was evaporated in vacuo. The remaining oil was dissolved in water followed by extraction of unreacted ester with tert-butyl methyl ether (TBME) (ee$_{ester}$=87%, determined as in Example 2). The water phase was acidified to pH=3 and the acid extracted with TBME. After drying over Na$_2$SO$_4$ and evaporation of the TBME, 1.8 g (2S)-2-Ethoxy-3-(4-hydroxyphenyl)propanoic acid was obtained as an oil, which crystallized on standing (m.p.=105° C., ee$_{acid}$=>99%, determined as in Example 2).

Example 4

Purification of the Esterase

Fermentation of Asperqillus oryzae IFO4177

Fed batch fermentation of a derivative of Aspergillus oryzae IFO4177 was performed in a medium comprising maltodextrin as a carbon source, urea as a nitrogen source and yeast extract. The fed batch fermentation was performed by inoculating a shake flask culture of A. oryzae into a medium comprising 3.5% of the carbon source and 0.5% of the nitrogen source. After 24 hours of cultivation at pH 5.0 and 34° C. the continuous supply of additional carbon and nitrogen sources were initiated. The carbon source was kept as the limiting factor and it was secured that oxygen is present in excess. The fed batch cultivation was continued for 4 days, after which the enzyme was recovered by centrifugation, ultrafiltration, filtration, germ filtration and spray drying.

Assay for Ester Hydrolysis:

The assay is an pH indicator based assay, where the decrease in pH is measured with p-Nitrophenol, when the enzyme cleaves the ester Ethyl (2RS) (+/−) 2-ethoxy-3-(4-hydroxyphenyl)propanoate. The buffer capacity of the enzyme sample in question has to be low, as a high buffer capacity in the sample will suppress the pH drop.

50 µl enzyme (diluted in 5 mM BES (Sigma B-6420), pH 7.1) was mixed with 100 µl Assay solution (a mixture of 400 µl Ethyl (2RS) (+/−) 2-ethoxy-3-(4-hydroxyphenyl)propanoate (55 mM in acetonitril), 2000 µl 5 mM p-Nitrophenol in 5 mM BES, pH 7.1 and 7600 µl 5 mM BES, pH 7.1). After a 5 minutes lag period, the decrease in OD$_{405}$ the next 10 minutes was monitored as a measurement of the enzyme activity. If the slope of the monitored curve deviated from linearity, the assay was repeated with a higher enzyme dilution.

Purification of the Esterase 24 g of a spray dried Aspergillus oryzae IFO4177 supernatant was dissolved in 375 ml 5 mM CH$_3$COOH/NaOH, pH 4.0 and the pH was adjusted to pH 4.0. The solution had a 1 mS/cm conductivity. The solution was applied to a 100 ml S-sepharose FF column (Amersham Pharmacia Biotech) equilibrated in 25 mM CH$_3$COOH/NaOH, pH 4.0. After washing the column with the same buffer, the column was eluted with a linear NaCl gradient from 0 to 0.5M over 5 column volumes. Fractions (10 ml) from the column were analyzed for esterase activity and fractions 42–46 were pooled. The 42–46 pool was dialysed over night against 10 mM KH$_2$PO$_4$/NaOH, pH 7.0 in dialysis tubing and then applied to a 40 ml Q-sepharose FF column (Amersham Pharmacia Biotech) column equilibrated in 20 mM KH$_2$PO$_4$/NaOH, pH 7.0. After washing the column with the same buffer, the column was eluted with a linear NaCl gradient from 0 to 0.25M over 5 column volumes. Fractions from the column were analysed for activity. The activity was found in the unretained fraction. The pH of the unretained fraction was adjusted to pH 8.0 and applied to the same 40 ml Q-sepharose FF column, but this time equilibrated in 20 mM HEPES/NaOH, pH 8.0. After washing the column with the HEPES buffer, the column was eluted with a linear NaCl gradient from 0 to 0.25M over 5 column volumes. Fractions (4 ml) from the column were analysed for activity and fractions 18–22 were pooled. The 18–22 pool was diluted 10 times with deionised water and applied to an 8 ml SOURCE Q column (Amersham Pharmacia Biotech) equilibrated in 20 mM HEPES/NaOH, pH 8.0. After washing the column with the same buffer, the column was eluted with a linear NaCl gradient from 0 to 150 mM over 30 column volumes. Fraction (3 ml) 28 and 29 was pooled and applied to a 300 ml Superdex75 column (Amersham Pharmacia Biotech) equilibrated in 20 mM HEPES/NaOH, 200 mM NaCl, pH 8.0. The Superdex75 column was eluted with the same buffer and fractions (5 ml) were analyzed for activity. The enzyme activity peaked in fraction 6 and 7. Fraction 5, 6, 7 and 8 were concentrated to approx. 70 µl in 10 kDa cut-off polysulfone Ultrafuge units (ultrafiltration by centrifugation). 10 µl of each fraction were applied to a SDS-PAGE gel, and it was seen that the intensity of a ~70 kDa band followed the activity. Fraction 6 and 7 were used for cleavage and Edman protein sequencing.

Example 5

Cleavage of the Esterase into Fragments and Sequencing of the Fragments

Reduction and Alkylation

75 µl of the purified enzyme sample was mixed with 75 µl SDS PAGE sample buffer with DTT and incubated at 37° C. for 20 min. The sample was heated to 95° C. for 3 min, cooled and subsequently 20 µl 1M Iodoacetamide (in 0.5M Tris pH 9.2) was added. Incubation for 20 min at room temperature.

In-Gel Digestion

Nine lanes in a Novex SDS-PAGE gel were loaded with the sample (all). After running the gel it was stained according to standard procedures from Novex. Pieces of the gel holding the ~70 kDa band was subsequently cut out and minced with a blade. The gel pieces was washed 2× in 0.5M Tris pH 9.2/Acetonitrile (ACN) (1:1) for 45 min at 37° C. The gel pieces were treated with 100% ACN for 10 min to introduce shrinking of the pieces. The ACN was removed and the pieces dried in a speed-Vac. 200 µl 0.1M ($NH_4$)$HCO_3$ was added and incubated for 15 min. The ($NH_4$)$HCO_3$ was removed and 100 µl ACN added. Again incubation for 10 min followed by removal of ACN and drying in a speed-vac. The cycle with alternating ($NH_4$)$HCO_3$ and ACN addition/removal was repeated 2×. After the last drying step 25 µl 0.1 µg/µl Acromobacter lysyl endopeptidase in 0.1M Tris pH 9.2, 10% ACN was added. Incubation for 20 min. Then 350 µl 0.1M Tris pH 9.2, 10% ACN was added. Incubation was continued over night at 37° C.

Then 40 µl 10% Trifluoroacetic acid (TFA) was added and after a 10 min incubation, the supernatant was removed (saved for control). Extraction of peptides was done 2× by adding 200 µl 0.1% TFA, 60% ACN to the gel pieces and incubate for 45 min at 37° C. All extracts were collected (65 µl+200 µl+200 µl) and concentrated in the speed-vac to 50 µl. 50 µl 0.1% TFA was added and the sample re-dried to 50 µl.

Separation of Peptides

The sample was run on RP-HPLC on a 2×50 mm Vydac C-18 column using a TFA/ACN solvent system (gradient from 0% to 64% ACN in 0.1% TFA over 31 min, 150 µl/min, detection at 214 nm). Controls with blank gel pieces were run in parallel. Selected peptides from the separation were subjected to sequence analysis by Edman degradation.

Peptide Sequences

Sequence analysis of the peptides showed that three sequences was obtained. The determined sequences were denoted 161299Afr15 (SEQ ID NO: 3), 161299Afr17 (SEQ ID NO: 4) and 161299Afr23 (SEQ ID NO: 5).

Example 6

Cloning of the Esterase Gene

Partial Cloning of the Esterase Gene by PCR.

The three peptide sequences determined in example 5 were all found to show some homology to a Penicillin V amidohydrolase from *Fusarium oxysporum* (GeneSeqP: W00290). Thus, 161299Afr15 (SEQ ID NO: 3), 161299Afr17 (SEQ ID NO: 4) and 161299Afr23 (SEQ ID NO: 5) could be aligned with amino acids 381–398, 349–366 and 181–201, respectively, of GeneSeqP: W00290.

Based on this alignment, two PCR primers were designed to PCR amplify a part of the *A. oryzae* esterase gene.

A primer (B2716F09, SEQ ID NO: 6) corresponding to the sense direction protein sequence of peptide 161299Afr23 (amino acids 13–21 of SEQ ID NO: 5) was synthesized.

A primer (B2716F11, SEQ ID NO: 7) corresponding to the antisense direction of the protein sequence of peptide 161299Afr15 (amino acids 4–12 of SEQ ID NO: 3) was synthesized.

These two PCR primers were used for amplification of an esterase gene fragment in the following way:

Genomic DNA was prepared from *Aspergillus oryzae* IFO 4177 as described by Yelton et. al. (M. M. Yelton, J. E. Mamer and W. E. Timberlake (1984) *Proc. Natl. Acad. Sci. USA* 81, 1470–1474).

The Expand PCR system (Roche Molecular Biochemicals, Basel, Switzerland) was used for the amplification following the manufacturers instructions for this and the subsequent PCR amplifications. The magnesium concentration was held at 2.5 mM in all PCR reactions.

The following thermal cycling program was run on an MJ Research PTC 150 thermal cycler:

| | |
|---|---|
| 94° C. for 1 min. | 1 cycle |
| 94° C. for 10 sec. | |
| Temperature ramping at −0.5° C./sec. | |
| 50° C. for 10 sec. | 40 cycles |
| 72° C. for 30 sec. | |
| 72° C. for 1 min. | 1 cycle. |

A PCR product of approx. 550 bp were detected on a 1% agarose gel. This fragment was recovered and cloned into the pCR4-TOPO vector following the manufacturers instructions (Invitrogen BV, Groningen, the Netherlands).

A plasmid with an insert of the expected size, pCaHj571, was selected for sequencing and it was sequenced using the following primers: −48 reverse (SEQ ID NO: 8) and −40 universal (SEQ ID NO: 9).

All sequence reactions were made using BigDye™ Terminator Cycle Sequencing Kits from the Perkin-Elmer Corporation (USA), and the reactions were run on an ABI 3700 capillary sequencer from the Perkin-Elmer Corporation following the manufacturers instructions.

The sequence encoded a protein sequence homologous to the *F. oxysporum* amidohydrolase and also encoded the peptide sequence 161299Afr17, and it was thus concluded that the amplified fragment is a part of the esterase gene. The sequence of the PCR fragment is shown as SEQ ID NO: 27.

Genomic Cloning of the Esterase Gene.

A cosmid library of *A. oryzae* IFO4177 has previously been prepared as described in WO 9801470.

The insert of pCaHj571 was labelled with DIG by using the plasmid as template in a PCR reaction together with the primers B2716F09 and B2716F11 and the PCR DIG probe synthesis kit from Roche Molecular Biochemicals following the manufacturers instructions.

The DIG labeled fragment was used to probe filters of the cosmid library using the recomandations of Roche Molecular Biochemicals, and the hybridization signals were visualized using CSPD detection following the instructions of Roche Molecular Biochemicals and using a LAS1000 plus CDC camera manufactured by Fujifilm.

One cosmid giving a clear hybridization signal was isolated and termed pCaHj577.

A southern blot using genomic DNA of *A. oryzae* IFO4177 was done using the same probe, hybridization conditions and detection method as for the cosmid isolation. The DNA was digested with the restriction enzymes BamH I, BglII, EcoR I, Hind III, Mlu I, Mun I, Sac I, SaL I or Xho I. In addition an Asp 718 digestion was made, and double digestions of Asp 718 and the list of enzymes just indicated was made.

The Southern blot indicated that the 5' end of the esterase gene was present on an approx. 1.4 kb Asp718 fragment. The 3' end of the gene appeared to be present on an approx 2 kb Mun I—EcoR I fragment.

The 5' and the 3' end of the gene was cloned by inverse PCR in the following way:

From the sequence given in SEQ ID NO: 27, the following PCR primers were designed: B2998F06 (SEQ ID NO: 10), B3591G12 (SEQ ID NO: 11) and B2998F07 (SEQ ID NO: 12).

For the 5' inverse PCR 500 ng of pCaHj577 was digested with Asp718, and the formed fragments were separated on a 1% agarose gel. Fragments of approx. 1.4 kb were recovered from the gel and dissolved in a total volume of 0.5 ml. Ligation buffer and T4 DNA ligase (Roche Molecular Biochemicals) was added and the solution was incubated at 16° C. for approx. 18 hours. The mixture was concentrated by ethanol precipitation and the ligation product was used as template in a PCR reaction using the primers B2998F06 and B3591G12 and the PCR conditions described in the previous section. A PCR product of approx. 1 kb was detected on a 1% agarose gel. This fragment was recovered and cloned into the pCR4-TOPO vector. Sequencing of one of the formed plasmids demonstrated the insert to be the 5' end of the esterase. This plasmid was named pCaHj578.

For the 3' inverse PCR 500 ng of pCaHj577 was digested with Mun I and EcoR I, and the formed fragments were separated on a 1% agarose gel. Fragments of approx. 2 kb were recovered from the gel and dissolved in a total volume of 0.5 ml. Ligation and concentration was done as with the 5' end. The ligation product was used as template in a PCR reaction using the primers B2998F06 and B2998F07. A PCR product of approx. 1.1 kb was detected on a 1% agarose gel. This fragment was recovered and cloned into the pCR4-TOPO vector. Sequencing of one of the formed plasmids demonstrated the insert to be the 3' end of the esterase. This plasmid was named pCaHj579.

Sequencing of the Esterase Gene.

The esterase gene was sequenced using the plasmids pCaHj571, pCaHj 577, pCaHj578 and pCaHj579 as templates and the following primers:
−48 reverse (SEQ ID NO: 8), −40 universal (SEQ ID NO: 9), B2998F06 (SEQ ID NO: 10), B3591G12 (SEQ ID NO: 11), B2998F07 (SEQ ID NO: 12), B3864E07 (SEQ ID NO: 13), B3864E08 (SEQ ID NO: 14), B3998D09 (SEQ ID NO: 15), B3998D10 (SEQ ID NO: 16), B3998D11 (SEQ ID NO: 17), and B3591G11 (SEQ ID NO:18).

All sequence reactions were made using BigDye™ Terminator Cycle Sequencing Kits from the Perkin-Elmer Corporation (USA), and the reactions were run on an ABI 3700 capillary sequencer from the Perkin-Elmer Corporation following the manufacturers instructions.

The sequence is shown together with the translation as SEQ ID NO: 1. A single intron was predicted by the computer programme NetGene2 (P. G. Korning. et. al (1996) Nucl. Acids. Res. 24: 3439–3452).

By analysis of the protein sequence a secretory signal sequence was predicted using the computer programme SignalP (H. Nielsen et al (1997) Protein Eng. 10: 1–6).

Example 7

Expression of the Esterase Gene

The *Aspergillus* expression plasmid pCaHj527 (WO 0070064) consists of an expression cassette based on the *Aspergillus niger* neutral amylase II promoter fused to the *Aspergillus nidulans* triose phosphate isomerase non translated leader sequence (Pna2/tpi) and the *Aspergillus niger* amyloglycosidase terminater (Tamg). Also present on the plasmid is the *Aspergillus* selective marker amdS from *Aspergillus nidulans* enabling growth on acetamide as sole nitrogen source and the URA3 marker from *Saccharomyces cerevisiae* enabling growth of the pyrF defective *Escherichia coli* strain DB6507 (ATCC 35673). Transformation into *E. coli* DB6507 using the *S. cerevisiae* URA 3 gene as selective marker was done in the following way:

*E. coli* DB6507 was made competent by the method of Mandel and Higa (Mandel, M. and A. Higa (1970) J. Mol. Biol. 45, 154). Transformants were selected on solid M9 medium (Sambrook et. al (1989) Molecular cloning, a laboratory manual, 2. edition, Cold Spring Harbor Laboratory Press) supplemented with 1 g/l casaminoacids, 500 μg/l thiamine and 10 mg/l kanamycin.

PCaHj527 was modified in the following way:

ThePna2/tpi promoter present on pCaHj527 was subjected to site directed mutagenises by a simple PCR approach.

Nucleotide 134–144 was altered from SEQ ID NO: 19 to SEQ ID NO: 20 using the mutagenic primer 141223 (SEQ ID NO: 21).

Nucleotide 423–436 was altered from SEQ ID NO: 22 to SEQ ID NO: 23 using the mutagenic primer 141222 (SEQ ID NO: 24).

The resulting plasmid was termed pMT 2188.

The esterase gene was cloned into pMT2188 in the following way:

The esterase gene was PCR amplified from pCaHj577 using the PCR conditions described in Example 6, except only 20 cycles was used. The primers were the following: B6093H05 (SEQ ID NO: 25) and B6093H03 (SEQ ID NO: 26).

Figure 1:
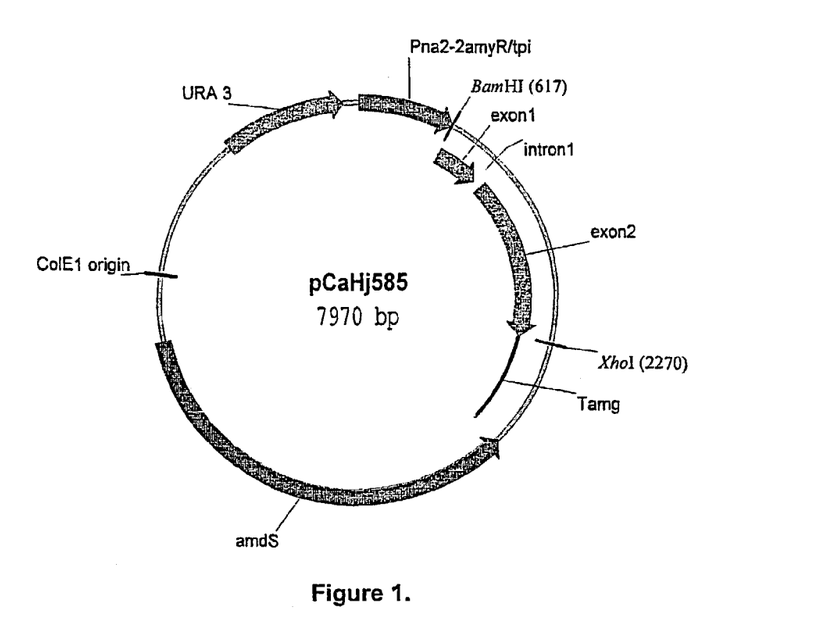
FIG. 1 shows a restriction map of the esterase expression plasmid pCaHj585.

The formed PCR fragment was digested with BamH I and Xho I, and the large fragment formed was ligated to pMT2188 digested with the same enzymes. The ligation mixture was transformed into *E. coli* DB6507. A plasmid from one of the colonies formed was confirmed to have the expected insert by restriction analysis and DNA sequencing. This plasmid was termed pCaHj585. A restriction map of pCaHj585 is shown in FIG. 1.

PCaHj585 was transformed into *Aspergillus oryzae* BECh2 (WO 0039322), fermented and recovered as described in WO 95/00636.

Example 8

Use of Esterase for Stereoselective Hydrolysis of Chiral Ester

Ethyl (2RS) (+/−) 2-ethoxy-3-(4-hydroxyphenyl)propanoate (0.5 g) was shaken with 60 mg of the lyophilised hydrolytic enzyme mixture from *Aspergillus oryzae* in 1 ml 1M phosphate buffer (pH=7) with organic co-solvents (according to the table below) at 27° C. The reaction mixture was poured into 20 ml MeOH after 4 h to stop the enzymatic reactions followed by analysis by the chiral CCE method 2.

| Co-solvent | Product$_{acid}$ (%) | (ee)$_{acid}$ (%) |
|---|---|---|
| Acetone/0.1 ml | 37 | 93 |
| Acetone/0.3 ml | 31 | 94 |
| THF/0.1 ml | 36 | 94 |
| THF/0.2 ml | 31 | 93 |
| THF/0.3 ml | 21 | 91 |
| 2-Propanol/0.1 ml | 36 | 97 |
| 2-Propanol/0.3 ml | 27 | 93 |
| Ethanol/0.1 ml | 35 | 96 |
| Ethanol/0.2 ml | 32 | 96 |
| Ethanol/0.3 ml | 22 | 93 |

In another experiment, ethyl (2R/S) (+/−) 2-ethoxy-3-(4-hydroxyphenyl)propanoate (5 g) was added to an aqueous 0.1 M phosphate buffer pH 7 (10 ml). 100 mg of the lyophilised hydrolytic enzyme mixture from *Aspergillus*

*oryzae* was added and the mixture was stirred for 18 hours at room temperature. During that time, the pH of the reaction mixture was kept constant at pH=6-8 by addition of NaOH. Most of the water was evaporated in vacuo. Methanol was added to the remaining slurry in order to stop the hydrolysis. The precipitate, which formed was filtered off and the methanol was evaporated in vacuo. The remaining oil was dissolved in water followed by extraction of unreacted ester with TBME (CCE method 2: $ee_{ester}$=87%). The water phase was acidified to pH=3 and the acid extracted with TBME. After drying over $Na_2SO_4$ and evaporation of the TBME, 1.8 g (2S)-2-Ethoxy-3-(4-hydroxyphenyl)propanoic acid was obtained as an oil, which crystallized on standing (m.p.=105° C., CCE method 2: $ee_{acid}$>99%).

The invention claimed is:

1. An isolated esterase which is:
   (a) a polypeptide which has at least 95% identity with a polypeptide having an amino acid sequence as the mature peptide shown in SEQ ID NO: 2;
   (b) a polypeptide which has at least 95% identity with a polypeptide encoded by an esterase encoding part of the DNA sequence cloned into a plasmid present in *Escherichia coli* deposit number DSM 13977; or
   (c) a polypeptide which is encoded by a nucleic acid sequence which hybridizes with a complementary strand of the nucleic acid sequence shown as nucleotides 629–911 and 971–2208 of SEQ ID NO: 1 in a solution of 5×SSC, 5× Denhardt's solution, 0.5% SDS and 100 micrograms/ml of denatured sonicated salmon sperm DNA, followed by hybridization in the same solution for 12 hours at approximately 60° C., followed by washing twice for 30 minutes in 2×SSC, 0.5% SDS at a temperature of at least 65° C.

2. The esterase of claim 1, which is native to a strain of *Aspergillus*.

3. The esterase of claim 1, which is native to a strain of *A. oryzae*.

4. The esterase of claim 1, which has an amino acid sequence which comprises the mature peptide shown in SEQ ID NO: 2.

5. The esterase of claim 1, which is encoded by an esterase encoding part of the DNA sequence cloned into a plasmid present in *Escherichia coli* deposit number DSM 13977.

6. The esterase of claim 1, which has an amino acid sequence which has at least 95% identity with a polypeptide encoded by an esterase encoding part of the DNA sequence cloned into a plasmid present in *Escherichia coli* deposit number DSM 13977.

7. The esterase of claim 1, which has an amino acid sequence which has at least 98% identity with a polypeptide encoded by an esterase encoding part of the DNA sequence cloned into a plasmid present in *Escherichia coli* deposit number DSM 13977.

8. The esterase of claim 1, which has an amino acid sequence which has at least 95% identity with the mature peptide shown in SEQ ID NO: 2.

9. The esterase of claim 1, which has an amino acid sequence which has at least 98% identity with the mature peptide shown in SEQ ID NO: 2.

10. The esterase of claim 1, which is encoded by a nucleic acid sequence which hybridizes with a complementary strand of the nucleic acid sequence shown as nucleotides 629–911 and 971–2208 of SEQ ID NO: 1 in a solution of 5×SSC, 5× Denhardt's solution, 0.5% SDS and 100 micrograms/ml of denatured sonicated salmon sperm DNA, followed by hybridization in the same solution for 12 hours at approximately 60° C., followed by washing twice for 30 minutes in 2×SSC, 0.5% SDS at a temperature of at least 65° C.

11. The esterase of claim 1, which is encoded by a nucleic acid sequence which hybridizes with a complementary strand of the nucleic acid sequence shown as nucleotides 629–911 and 971–2208 of SEQ ID NO: 1 in a solution of 5×SSC, 5× Denhardt's solution, 0.5% SDS and 100 micrograms/ml of denatured sonicated salmon sperm DNA, followed by hybridization in the same solution for 12 hours at approximately 60° C., followed by washing twice for 30 minutes in 2×SSC, 0.5% SDS at a temperature of at least 68° C.

12. A polynucleotide comprising a nucleic acid sequence which encodes the esterase of claim 1.

13. A method for stereoselective hydrolysis of a chiral ester, comprising treating the ester with the esterase of claim 1.

14. A polynucleotide which encodes an esterase and comprises
   (a) a nucleic acid sequence which has at least 95% identity with the nucleic acid sequence shown as nucleotides 629–911 and 971–2208 of SEQ ID NO: 1;
   (b) a nucleic acid which hybridizes with a complementary strand of the nucleic acid sequence shown as nucleotides 629–911 and 971–2208 of SEQ ID NO: 1 in a solution of 5×SSC, 5× Denhardt's solution, 0.5% SDS and 100 micrograms/ml of denatured sonicated salmon sperm DNA, followed by hybridization in the same solution for 12 hours at approximately 60° C., followed by washing twice for 30 minutes in 2×SSC, 0.5% SDS at a temperature of at least 65° C.; or (c) a complementary strand of (a) or (b).

15. A nucleic acid construct comprising the polynucleotide of claim 14 operably linked to one or more control sequences capable of directing the expression of the esterase in a suitable expression host.

16. A recombinant expression vector comprising the nucleic acid construct of claim 15, a promoter, and transcriptional and translational stop signals.

17. A recombinant host cell transformed with the nucleic acid construct of claim 15.

18. A method for producing an esterase comprising cultivating the host cell of claim 17 under conditions conducive to production of the esterase, and recovering the esterase.

* * * * *